(12) United States Patent
Radhakrishnan et al.

(10) Patent No.: US 8,920,490 B2
(45) Date of Patent: Dec. 30, 2014

(54) ENDOPROSTHESES

(75) Inventors: Rajesh Radhakrishnan, Maple Grove, MN (US); Liliana Atanasoska, Edina, MN (US); Scott R. Schewe, Eden Prairie, MN (US); Ken Merdan, Loretto, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 340 days.

(21) Appl. No.: 13/106,449

(22) Filed: May 12, 2011

(65) Prior Publication Data

US 2011/0282431 A1 Nov. 17, 2011

Related U.S. Application Data

(60) Provisional application No. 61/334,351, filed on May 13, 2010.

(51) Int. Cl.
*A61F 2/82* (2013.01)
*A61F 2/91* (2013.01)

(52) U.S. Cl.
CPC ........... *A61F 2/91* (2013.01); *A61F 2250/0068* (2013.01)
USPC .................... 623/1.42; 623/1.39; 623/1.44

(58) Field of Classification Search
USPC ............. 623/1.38, 1.39, 1.4, 1.42, 1.43, 1.44, 623/1.45, 1.46
See application file for complete search history.

(56) References Cited

U.S. PATENT DOCUMENTS

| | | | |
|---|---|---|---|
| 5,091,205 A | 2/1992 | Fan | |
| 6,290,721 B1 | 9/2001 | Heath | |
| 6,334,856 B1 * | 1/2002 | Allen et al. | 604/191 |
| 7,575,593 B2 * | 8/2009 | Rea et al. | 623/1.42 |
| 2002/0082680 A1 * | 6/2002 | Shanley et al. | 623/1.16 |
| 2002/0144757 A1 | 10/2002 | Craig et al. | |
| 2003/0018380 A1 | 1/2003 | Craig et al. | |
| 2003/0077200 A1 | 4/2003 | Craig et al. | |
| 2004/0143317 A1 | 7/2004 | Stinson et al. | |
| 2005/0060021 A1 * | 3/2005 | O'Brien et al. | 623/1.15 |
| 2005/0070990 A1 | 3/2005 | Stinson | |
| 2005/0131532 A1 * | 6/2005 | Sirhan et al. | 623/1.42 |
| 2005/0192657 A1 | 9/2005 | Colen et al. | |
| 2005/0203613 A1 * | 9/2005 | Arney et al. | 623/1.42 |
| 2005/0216074 A1 | 9/2005 | Sahatjian et al. | |
| 2006/0038027 A1 | 2/2006 | O'Connor et al. | |
| 2006/0153729 A1 | 7/2006 | Stinson et al. | |
| 2008/0004691 A1 | 1/2008 | Weber et al. | |
| 2008/0294236 A1 | 11/2008 | Anand et al. | |
| 2008/0294246 A1 | 11/2008 | Scheuermann et al. | |
| 2009/0018647 A1 | 1/2009 | Benco et al. | |
| 2009/0123517 A1 | 5/2009 | Flanagan et al. | |

OTHER PUBLICATIONS

Kesapragada et al., "Two-component nanopillar arrays grown by Glancing Angle Deposition," Thin Solid Films, vol. 494, pp. 234-239, (2006).

Khandare et al., "Polymer—drug conjugates: Progress in polymeric prodrugs," Progress in Polymer Science, vol. 31, pp. 359-397, (2006).

Hoste et al., "New derivatives of polyglutamic acid as drug carrier systems," Journal of Controlled Release, vol. 64, pp. 53-61, (2000).

Li et al., "Polymer-drug conjugates: Recent development in clinical oncology", Advanced Drug Delivery Reviews, vol. 60, pp. 886-898, (2008).

Schetsky, "Shape Memory Alloys", Encyclopedia of Chemical Technology (3rd ed.), John Wiley & Sons, vol. 20, pp. 726-736, (1982).

\* cited by examiner

*Primary Examiner* — David Isabella
*Assistant Examiner* — Suba Ganesan
(74) *Attorney, Agent, or Firm* — Fish & Richardson P.C.

(57) ABSTRACT

A medical device is provided with a porous region including a reservoir zone including a polymer and a protective zone between adjacent tissue and the reservoir zone that restricts the tissue from direct contact with the polymer.

23 Claims, 5 Drawing Sheets

ENDOPROSTHESES

CROSS-REFERENCE TO RELATED APPLICATION

This application claims priority under 35 USC §119(e) to U.S. Provisional Patent Application Ser. No. 61/334,351, filed on May 13, 2011, the entire contents of which are hereby incorporated by reference.

TECHNICAL FIELD

This invention relates to endoprostheses.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath U.S. Pat. No. 6,290,721, the entire contents of which are hereby incorporated by reference herein.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

In one aspect, the invention features a stent. The stent comprises a porous region having a surface and a thickness, reservoir zone in the porous region including a therapeutic agent and a polymer, and a protective zone in the porous region that is substantially free of polymer. The protective zone extends from the surface to a depth about 50 nm or more. The porous region includes pore openings at the surface. The pore openings are formed among a series of posts or pillars and having a width of about 300 nm or less.

Embodiments may include one or more of the following features. The protective zone has a different surface energy or hydrophilicity than the reservoir zone. The porous region is formed of ceramic or metal. The porous region is formed of one or more of Ti, chromium, iridium, aluminum, tantalum, zirconium, platinum, niobium, magnesium, iron, zinc, oxides thereof, calcium phosphate, or hydroxyapatite. The porous region has a thickness of about 0.5 micron to 10 microns. The protective zone extends about 5-500 nm from the surface. The porous region has a thickness of about 10-500 nm. The pore opening width is about 10-100 nm. The series of posts or pillars are substantially linearly parallel posts or pillars having a height of about 0.5 to 10 µm and a spacing of about 1 to 250 nm. The posts are provided on a surface of a stent body and the posts are substantially parallel to the surface. The posts are provided on a surface of a stent body and the posts are at an angle with respect to the body. The porous region includes a loading port communicating with the reservoir zone such that drug and polymer can be loaded directly into the reservoir zone. The loading port includes an opening on the surface of the porous region, the opening having a width greater than the width of the pore openings. The loading port includes a cap over the opening of the loading port. The protective zone includes a therapeutic agent. The polymer is a biostable polymer. The polymer is a bioerodible polymer. The therapeutic agent in the reservoir zone includes a gradient concentration distribution along a length of the pore openings. The polymer and the therapeutic agent in the reservoir zone include a gradient ratio distribution of the concentration of the therapeutic agent to the concentration of the polymer across a cross-section of at least one pore opening.

In another aspect, the invention features a method. The method comprises providing a stent including a porous region having a surface and a thickness, forming a reservoir zone by disposing a therapeutic agent and polymer in the porous region, and providing a protective zone that is substantially free of polymer. The porous region has pore openings at the surface. The pore openings are formed among a series of posts or pillars and have a width of about 300 nm or less. The protective zone extends from the surface to a depth of about 50 nm or more.

Embodiments may include one or more of the following features. Forming the reservoir and protective zone includes selecting the relative surface energy or hydrophobicity of the zones. Forming the reservoir protective zones includes delivering therapeutic agent and drug directly to the reservoir zone. Forming the reservoir and protective zones includes removing polymer from the protective zone.

In another aspect, the invention features an implantable medical device for use in contact with tissue. The medical device comprises a porous region having a surface and a thickness, a reservoir zone including a therapeutic agent or polymer, a protective zone extending from the surface to the reservoir zone, and a loading port in communication with the reservoir zone. The porous region has pore openings at the surface. The loading port includes an opening larger than a width of the pore openings in the porous region, and in use. The loading port is in contact with a body tissue without having substantially any polymer in contact with the body tissue.

Embodiments may include one or more of the following features. The medical device also comprises a cap to cover the opening of the loading port. The loading port is substantially free of the polymer.

In another aspect, the invention features a method. The method comprises providing a stent including a porous region having a surface and a thickness, loading into the porous region a therapeutic agent and polymer from an opening of a loading port in communication with the porous region, providing a protective zone that is substantially free of polymer, and providing a cap to the opening of the loading port or removing the polymer from the opening of the loading port to prevent tissue contacting with the polymer in the opening of the loading port during use. The porous region has pore openings at the surface Embodiments may include one or more of the following features. The opening of the loading port has a larger width than the widths of the pore openings in the porous region. The cap is welded or friction fit into the opening after loading the therapeutic agent and the polymer. The cap polymer is removed mechanically or using laser ablation.

Embodiments may include one or more of the following advantages. A stent can be provided with a drug in polymer matrix that is protected from abrasion during handling and delivery into the body. The polymer and drug can be held in a reservoir zone, which is below the surface of a porous region. The reservoir zone can be spaced from the surface by a protection zone such that the polymer cannot be easily contacted during handling. The protection zone can be such that the polymer does not contact tissue of the lumen wall upon implantation of the stent, avoiding the potential physiological irritation or inflammation by tissue-polymer contact. These advantages are enjoyed using a porous region having nanometer size pore widths, and micron size pore depths, such that substantial quantities of polymer and drug can be incorporated and drug release can be modulated by the pore openings. The structure can be effectively manufactured. For example, the drug and polymer can be loaded directly into the reservoir zone without passing through the protection zone. The protection zone and/or the reservoir zone can be selected to discourage polymer from the protection zone and encourage polymer to remain in the reservoir zone by, for example, controlling the relative surface tension, surface energy, or hydrophobicity of the zones.

DETAILED DESCRIPTION

Figure 1:
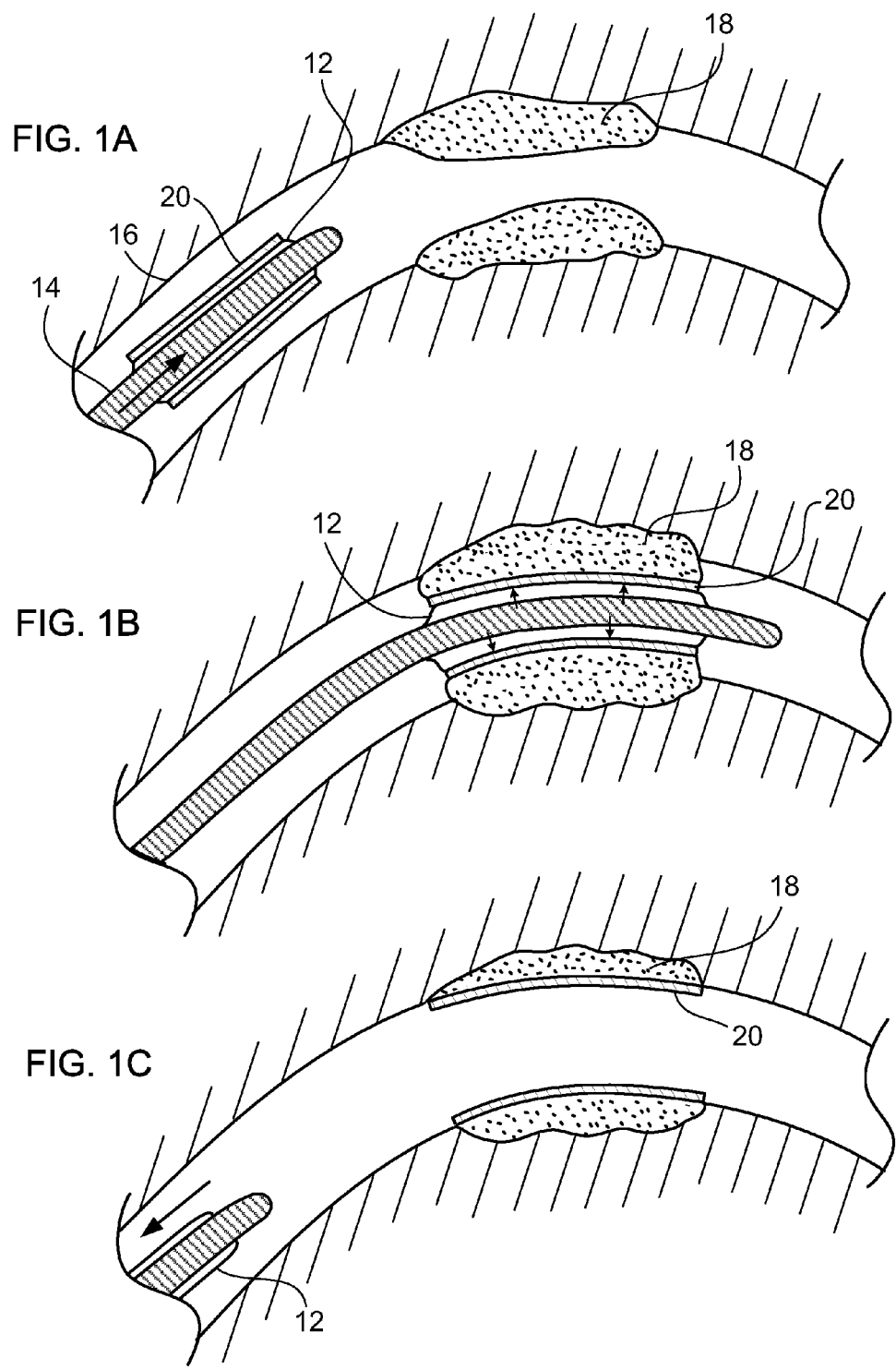
FIGS. 1A-1C are longitudinal cross-sectional views illustrating delivery of a stent in a collapsed state, expansion of the stent, and deployment of the stent.

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2:
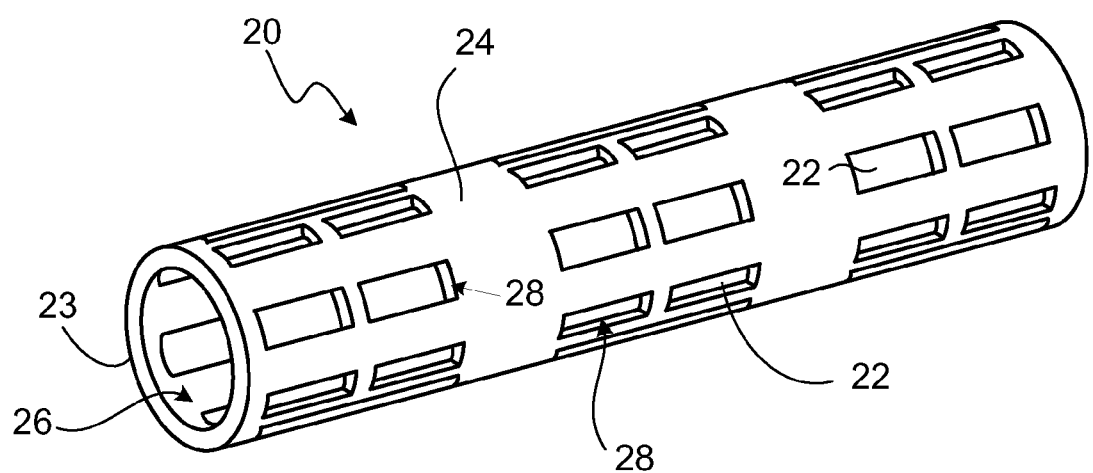
FIG. 2 is a perspective view of a stent.

Referring to FIG. 2, the stent 20 includes a plurality of fenestrations 22 between struts defined in a wall 23. Stent 20 includes several surface regions, including an outer, or abluminal, surface 24, an inner, adluminal, surface 26, and a plurality of cutface surfaces 28. The stent can be balloon expandable, as illustrated above, or self-expanding stent. Examples of stents are described in Heath '721, supra.

Figure 3A:
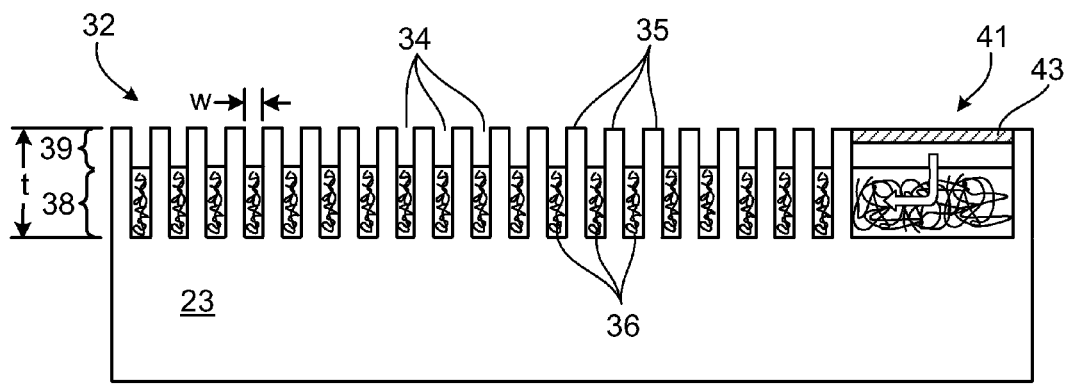
FIG. 3A is a cross sectional view through a stent strut.
Figure 3B:
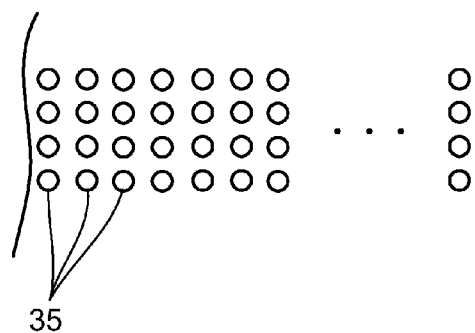
FIG. 3B is a plan view of the surface of a stent strut.

Referring to FIGS. 3A and 3B, a cross section through and a plan view of a stent strut, the stent wall 23 includes on its abluminal side a porous region 32 having pore openings 34 on the abluminal surface. In the embodiment illustrated, the porous region is formed by a series of generally parallel adjacent pillars 35. Within the porous region is a therapeutic agent in a polymer matrix 36. The pores in the porous region have a pore opening width, w, at the surface that is typically in the nanometer range and a thickness, t, typically in the micron range. The drug/polymer matrix is disposed in a the porous region in a reservoir zone 38 which is spaced from the abluminal surface by a protection zone 39, which is substantially free of polymer. The depth of the protection zone and the size of the pore openings are selected to protect the drug/polymer matrix during handling and delivery into the body, and to restrict the tissue from substantial polymer-tissue contact at the treatment site.

Figure 4A:
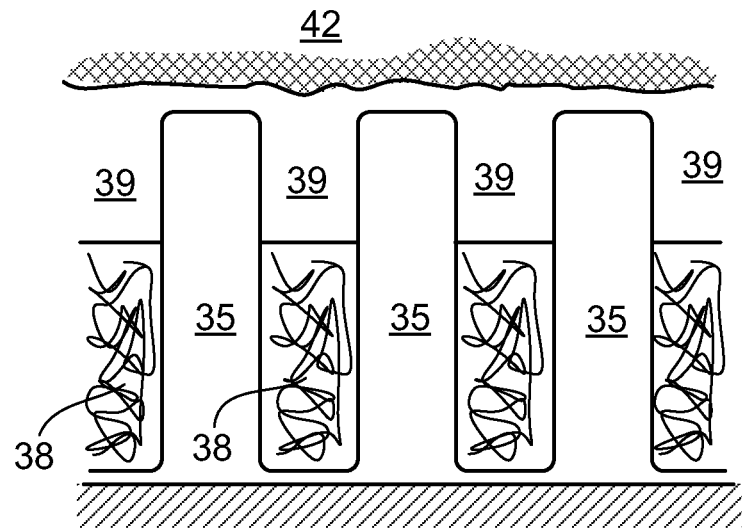
FIGS. 4A-4B are cross-sectional views of porous regions.
Figure 4B:
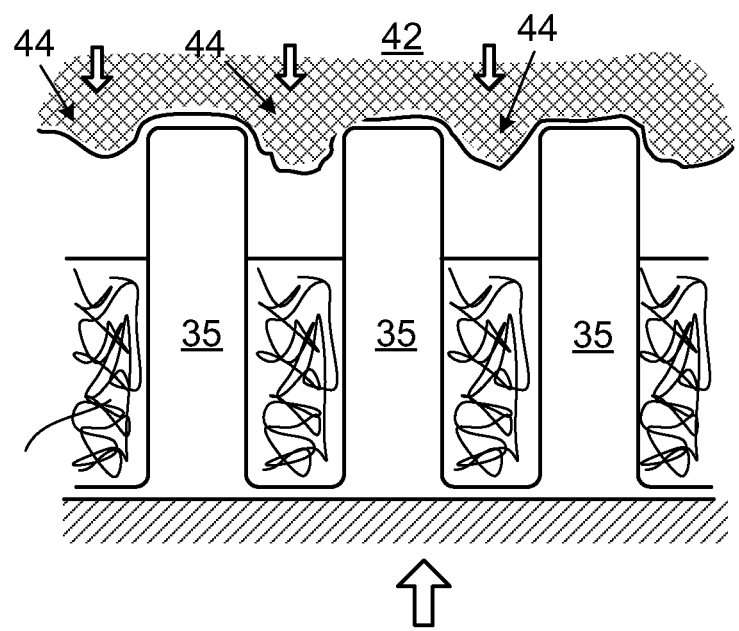

Referring to FIG. 4A, which depicts a greatly enlarged cross section of the porous region, the stent, in use, is delivered into the body to a treatment site and expanded into contact with the tissue 42. Referring particularly to FIG. 4B, as the stent is pressed (lower arrow) against the tissue 42 during implantation, portions 44 of the tissue can enter the pore openings (upper arrow) but do not extend beyond the protection zone into direct contact with the polymer in the reservoir zone.

In embodiments, the pore width, w, is in the range of about 1-300 nm, e.g., about 10-100 nm. In embodiments, the depth of the protection zone is about equal to or greater than the pore width, e.g. about twice, five times, ten times the pore width or more. In addition, the protection zone 39 can be about 5% or more, e.g., 10 or 25% or more of the thickness, t, of the porous region 32. The protection zone 39 has, in embodiments, depth from the surface of the porous region of about 5 nm or more, e.g., about 50-150 nm or more. The overall pore depth from the abluminal surface and the thickness of the reservoir zone are selected to permit sufficient drug to be loaded into and eluted from the stent. In embodiments, the porous region thickness, t, of about 0.5-10 microns. The thickness of the reservoir zone is about 90% or less of the pore depth. In embodiments in which the porous region is formed of posts or pillars, the post width can be larger or smaller than the pore width.

Referring back to FIGS. 3A and 3B, the polymer and drug can be loaded directly into the reservoir zone, without passing through the protective zone, through a port 41 adjacent to, e.g., laterally adjacent to, and in fluid communication with the porous region 32. The port has an opening substantially wider than the pore openings through which a polymer, e.g., in a solvent, or a polymer precursor, such as a monomer, with or without a drug, can be delivered. The polymer (or polymer with a drug) then flows laterally (arrow) into the reservoir zone. The port 41 can be provided with a cap 43, e.g., of metal such as stainless steel, to restrict the tissue from contact with the polymer during use. In some implementations, the cap 43 can be made of a polymer that is biocompatible (e.g., more biocompatible than the polymer carrying the drug). The cap 43 can be spot welded or friction fit into place after loading the polymer into the porous region. In embodiments, the cap can be provided with apertures (not shown) sized to allow drug to elute from the port area while restricting the tissue from direct contact with the polymer. In embodiments, the port opening has a width of about 1 micron or more, e.g., about 10 micron or more.

In some embodiments, after the polymer or polymer/drug mixture is loaded into the reservoir zone, materials, e.g., the polymer carrying the drug, remaining in the port 41 and/or the nearby region are removed so that in use, body tissues do not directly contact with the drug-carrying polymer. The materials can be removed mechanically, via laser ablation, or using other methods.

The viscosity of the polymer/drug mixture can be adjusted, i.e. reduced, to encourage lateral flow in the reservoir zone. After the mixture has been loaded, heat and/or vacuum can be applied to crosslink or remove any solvent. In other embodiments, the polymer/drug can be loaded into the reservoir zone through the pore openings. The drug/polymer mixture can be drawn into the pore opening by an electrical potential (inducing an electrostatic or electrochemical potential), vacuum, or hydrophilicity of the porous region. Any polymer remaining in the protection zone can be removed by, for example, washing with a solvent.

Figure 5:
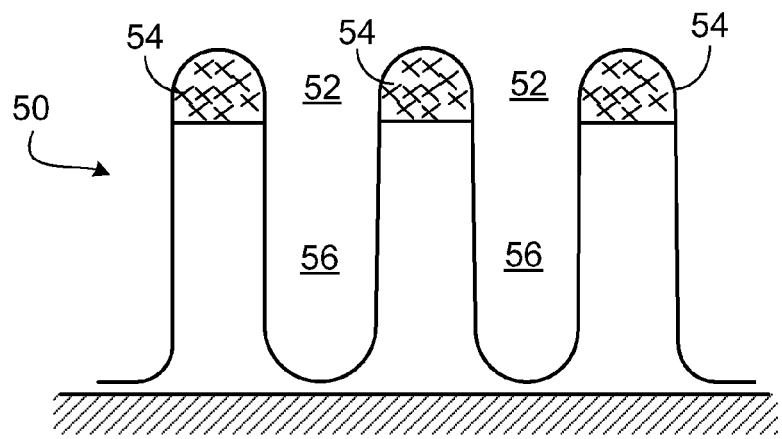
FIG. 5 is a cross-sectional view of a porous region.

Referring to FIG. 5, a porous region 50 can be constructed to discourage the presence of the polymer in the protection zone and encourage the polymer to remain in the reservoir zone. The porous region includes a protection zone 52 that has been treated to have decreased hydrophilicity or surface energy on the surface 54 of the porous channels compared to the reservoir region 56. The decreased hydrophilicity discourages the retention of polymer or organic solvent. The hydrophilicity or hydrophobicity of the pore surfaces in the protective zone hydrophobicity can be adjusted by, for example, modifying the type of material used in the protection region or adjusting the surface chemistry of the material, e.g., through exposure to radiation, e.g., cross-linking by e-beam, UV light, thermal heating, or others. Adjustment of hydrophobicity of certain ceramic materials by radiation is described in U.S. Patent Publication No. 2008/0004691. In other embodiments, a coating, e.g., a polymer can be provided by adjust hydrophobicity. Suitable polymers include polypyrolles loaded with fluoro-based doping anions. Alternatively, or in addition, the hydrophobicity or surface energy characteristic of the reservoir zone can be adjusted. The adjustment can be done using the same or a different method that is used for the protective zone. The adjustment of the hydrophilicity or hydrophobicity of the pore surfaces, in the protective zone and/or in the reservoir zone, can control the distribution of the therapeutic agent in the reservoir zone. For example, the therapeutic agent in the pores can have a gradient concentration distribution along a length of the pores. In another example, the polymer and the therapeutic agent in the reservoir zone include a gradient ratio distribution of the concentration of the therapeutic agent to the concentration of the polymer across a cross-section of at least one pore, e.g., from the center of the pore to the pore edge. The therapeutic agent can be controlled to provide a sustaining drug release and be restricted from bursting.

In embodiments, a modified silane can be bonded to the porous region in the protective and reservoir zone to adjust surface energy. Modified silanes are discussed in U.S. Patent Publication No. 2009/0018647.

Figure 6:
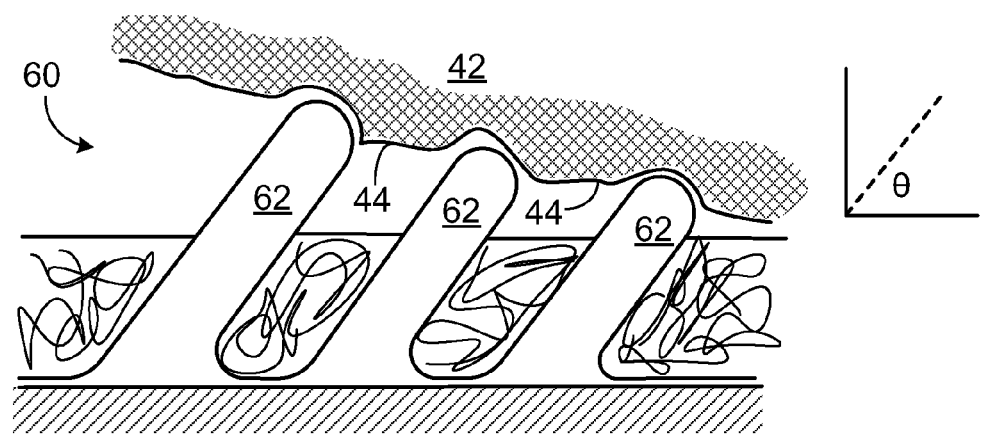
FIG. 6 is a cross-sectional view of a porous region.

Referring to FIG. 6, a porous region 60 is formed of substantially parallel posts 62 that are at an angle, θ, to the stent body. The angle θ, along with the pore opening width and the protection zone depth, is selected to restrict the tissue 44 from directly contacting polymer in the reservoir zone. In particular, a smaller angle θ, discourages entry of tissue through the pore openings. In embodiments, the angle θ is about 80° or less, e.g., about 60° or less. In other embodiments, the posts or pillars 62 are non-parallel to each other (not shown in the figure), for example, irregularly or randomly oriented. The non-parallel posts can produce pores that have a large base and a small opening. Openings formed among the posts can have nanometer widths and micron depths.

The porous region can be formed of a nonpolymeric material such as a metal or a ceramic as a layer on a stent body or directly in the stent body. Suitable metals include, for example, titanium, aluminum, chromium, iridium, various radiopaque metals and alloys. Suitable ceramics include oxides of these metals, e.g. iridium oxide or titanium oxide. The porous region can be formed, for example, by deposition and/or removal techniques. In embodiments, the porous region is formed by the GLAD process in which particles are deposited at defined angles to form selected surface structures. The GLAD process is described further in S. V. Kesapragada et al. Thin Solid Films 494 (2006) 234 and U.S. Patent Publication No. 2009/0123517. The porous region can also be formed by anodization, described in U.S. Patent Publication Nos. 2005/0060021 and 2005/0192657. The porous region can have structures other than linear posts or pillars. For example, the porous regions can include tortuous interconnecting pathways. In embodiments, the porous region can be a ceramic, e.g. IROX which is deposited by physical vapor deposition, as described in U.S. Patent Publication Nos. 2008/0294236 and 2008/0294246. In particular embodiments, the ceramic can be characterized by a rough morphology of defined grains which includes between the grain voids into which polymer and drug can be deposited. In embodiments, the porous region can be formed by electrochemical etching, dealloying or laser drilling. The polymer and drug can be introduced by microfab, micropen, inkjet printing or dipping. The porous region can be used on medical devices other than stents, such as guidewires, catheters, valves, and cardiac rhythm management device components such as electrical leads for use in the vascular system.

Suitable polymers are biostable or bioerodible polymers. Drug eluting polymers may be hydrophilic or hydrophobic. Suitable polymers include, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenerated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS® (Boston Scientific Corporation, Natick, Mass.), and described in Dudash U.S. Pat. No. 5,091,205, the disclosure of which is hereby incorporated herein by reference, which describes medical devices coated with one or more polyisocyanates such that the devices become instantly lubricious when exposed to body fluids. In another preferred embodiment of the invention, the polymer is a copolymer of polylactic acid and polycaprolactone. Suitable polymers are discussed in U.S. Patent Publication No. 2006/0038027.

In embodiments, the polymer is capable of absorbing a substantial amount of drug solution. When applied as a coating on a medical device in accordance with the present invention, the dry polymer is typically on the order of from about 1 to about 50 microns thick. Very thin polymer coatings, e.g., of about 0.2-0.3 microns and much thicker coatings, e.g., more than 10 microns, are also possible. Multiple layers of polymer coating can be provided. Such multiple layers are of the same or different polymer materials. In embodiments, polymer-drug conjugates can be used. Suitable polymer conjugates are discussed in Khandare et al., Prog. Polym. Sci. 31, 359-397 (2006), Hoste et al., Journal of Controlled Release 64, 53-61 (2000), and Li et al., Advanced Drug Delivery Reviews 60, 886-898 (2008). Polymer-drug conjugates are also described in Boston Scientific Scimed, Inc. invention disclosure number 07-D1297, the entire content of which is incorporated herein. The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Patent Publication No. 2005/0216074. Polymers for drug elution coatings are also disclosed in U.S. Patent Publication No. 2005/019265. A functional molecule, e.g. an organic, drug, polymer, protein, DNA, and similar material can be incorporated into groves, pits, void spaces, and other features of the ceramic.

The stent can be biostable or bioerodible. Suitable bioerodible materials include magnesium, iron, biodegradable polymers such as PLA, polycarbonate, and others. Suitable biostable materials include, for example, stainless steel. The stent can include (e.g., be manufactured from) metallic materials, such as stainless steel (e.g., 316L, BioDur® 108 (UNS S29108), and 304L stainless steel, and an alloy including stainless steel and 5-60% by weight of one or more radiopaque elements (e.g., Pt, Ir, Au, W) (PERSS®) as described in U.S. Patent Publication Nos. 2003/0018380, 2002/0144757, and 2003/0077200), Nitinol (a nickel-titanium alloy), cobalt alloys such as Elgiloy, L605 alloys, MP35N, titanium, titanium alloys (e.g., Ti-6A1-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. Patent Publication Nos. 2005/0070990 and 2006/0153729. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. Patent Publication No. 2004/0143317. The stents described herein can be configured for vascular, e.g., coronary and peripheral vasculature or non-vascular lumens. For example, they can be configured for use in the esophagus or the prostate. Other lumens include biliary lumens, hepatic lumens, pancreatic lumens, urethral lumens. The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., see U.S. Pat. No. 6,290,721).

All publications, patent applications, patents, and other references mentioned herein, are incorporated by reference herein in their entirety.

Other embodiments are within the following claims.

What is claimed is:

1. A stent comprising:

a porous region having a surface and a thickness, the porous region including pores having pore openings at the surface, the pores and the pore openings being formed among a series of posts or pillars and having a width of about 300 nm or less, a reservoir zone in the porous region, a portion of each of at least some pores forming a reservoir of the reservoir zone, each reservoir including a first therapeutic agent and a polymer, the portion being less than the entire pore, and a protective zone in the porous region that is substantially free of polymer, the protective zone comprising a porous channel having a pore surface defining an open protective volume over each reservoir, each open protective volume being another portion of the each of the at least some pores, and extending from the surface to a depth about 50 nm or more into the pores, wherein the porous region is configured such that the reservoir zone receives the first therapeutic agent and the polymer without the protective zone, including the pore surface in the protective zone, retaining a substantial amount of first therapeutic agent and the polymer, and wherein the porous region includes a loading port communicating with the reservoir zone such that drug and polymer is loaded directly into the reservoir zone without passing through the protective zone.

2. The stent of claim 1 wherein the protective zone has a different surface energy or hydrophilicity than the reservoir zone.

3. The stent of claim 1 wherein the porous region is formed of ceramic or metal.

4. The stent of claim 1 wherein the porous region has a thickness of about 0.5 micron to 10 microns.

5. The stent of claim 1 wherein the protective zone extends about 50-500 nm from the surface.

6. The stent of claim 1 wherein the porous region has a thickness of about 10-500 nm.

7. The stent of claim 1 wherein the pore opening width is about 10-100 nm.

8. The stent of claim 1 wherein the series of posts or pillars are substantially linearly parallel posts or pillars having a height of about 0.5 to 10 μm and a spacing of about 1 to 250 nm.

9. The stent of claim 1 wherein the posts are provided on a surface of a stent body and the posts are substantially parallel to the surface.

10. The stent of claim 1 wherein the posts are provided on a surface of a stent body and the posts are at an angle with respect to the body.

11. The stent of claim 1 wherein the polymer is a biostable polymer.

12. The stent of claim 1 wherein the polymer is a bioerodible polymer.

13. The stent of claim 1 wherein the first therapeutic agent in the reservoir zone includes a gradient concentration distribution along a length of the pore openings.

14. The stent of claim 1 wherein the polymer and the first therapeutic agent in the reservoir zone include a gradient ratio distribution of the concentration of the first therapeutic agent to the concentration of the polymer across a cross-section of at least one pore opening.

15. The stent of claim 1 wherein the loading port includes an opening on the surface of the porous region, the opening having a width greater than the width of the pore openings.

16. The stent of claim 15 wherein the loading port includes a cap over the opening of the loading port.

17. A stent comprising:
   a porous region having a surface and a thickness, the porous region including pores having pore openings at the surface, the pores and the pore openings being formed among a series of posts or pillars and having a width of about 300 nm or less,
   a reservoir zone in the porous region, a portion of each of at least some pores forming a reservoir of the reservoir zone, each reservoir including a first therapeutic agent and a polymer, the portion being less than the entire pore, and
   a protective zone in the porous region that is substantially free of polymer, the protective zone comprising a porous channel having a pore surface defining an open protective volume over each reservoir, each open protective volume being another portion of the each of the at least some pores, and extending from the surface to a depth about 50 nm or more into the pores,
   wherein the porous region is configured such that the reservoir zone receives the first therapeutic agent and the polymer without the protective zone, including the pore surface in the protective zone, retaining a substantial amount of first therapeutic agent and the polymer, and wherein the porous region is formed of one or more of Ti, chromium, iridium, aluminum, tantalum, zirconium, platinum, niobium, magnesium, iron, zinc, oxides thereof, calcium phosphate, or hydroxyaphatite.

18. The stent of claim 17 wherein the porous region includes a loading port communicating with the reservoir zone such that drug and polymer is loaded directly into the reservoir zone without passing through the protective zone.

19. The stent of claim 18 wherein the loading port includes an opening on the surface of the porous region, the opening having a width greater than the width of the pore openings.

20. The stent of claim 19 wherein the loading port includes a cap over the opening of the loading port.

21. An implantable medical device for use in contact with tissue comprising:
   a wall,
   a porous region on the wall, the porous region having a surface, a thickness, and pore openings at the surface,
   a reservoir zone in the porous region, the reservoir zone including a therapeutic agent or a polymer,
   a protective zone in the porous region and extending from the reservoir zone to the surface of the porous region, and
   a loading port on the wall and adjacent to the porous region, the loading port being in communication with the reservoir zone for loading the therapeutic agent or the polymer to the reservoir zone, and including an opening larger than a width of the pore openings in the porous region, and in use, the loading port being in contact with a body tissue without having substantially any polymer in contact with the body tissue, and the loading port and the porous region being configured such that the therapeutic agent or the polymer is loaded to the reservoir zone laterally from the loading port without passing through the protective zone.

22. The implantable medical device of claim 21, further comprising a cap to cover the opening of the loading port.

23. The implantable medical device of claim 21, wherein the loading port is substantially free of the polymer.

* * * * *